(12) United States Patent
Ho et al.

(10) Patent No.: US 9,400,923 B2
(45) Date of Patent: Jul. 26, 2016

(54) PATIENT INTERFACE IDENTIFICATION SYSTEM

(71) Applicant: KONINKLIJKE PHILIPS N.V., Eindhoven (NL)

(72) Inventors: Peter Chi Fai Ho, Pittsburgh, PA (US); Dmitry Nikolayevich Znamenskiy, Eindhoven (NL); Richard Andrew Sofranko, Finleyville, PA (US)

(73) Assignee: KONIKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/413,433

(22) PCT Filed: Jul. 11, 2013

(86) PCT No.: PCT/IB2013/055707
§ 371 (c)(1),
(2) Date: Jan. 8, 2015

(87) PCT Pub. No.: WO2014/009914
PCT Pub. Date: Jan. 16, 2014

(65) Prior Publication Data
US 2015/0193650 A1 Jul. 9, 2015

Related U.S. Application Data

(60) Provisional application No. 61/670,270, filed on Jul. 11, 2012.

(51) Int. Cl.
| G06K 9/00 | (2006.01) |
| A61M 16/06 | (2006.01) |
| G06K 9/62 | (2006.01) |
| A62B 18/02 | (2006.01) |
| A61M 16/00 | (2006.01) |

(52) U.S. Cl.
CPC ........... *G06K 9/00261* (2013.01); *A61M 16/06* (2013.01); *G06K 9/00221* (2013.01);
(Continued)

(58) Field of Classification Search
USPC ......... 382/100, 103, 106–108, 123, 140–141, 382/154, 168, 173, 181, 193, 199, 203, 209, 382/219, 232, 254, 266, 274–276, 285–294, 382/305, 312, 321, 224, 128–134; 128/206.21, 205.25, 848, 207.15
See application file for complete search history.

(56) References Cited

U.S. PATENT DOCUMENTS

| 7,274,822 B2 * | 9/2007 | Zhang ............... G06F 17/30265 382/224 |
| 2006/0023228 A1 | 2/2006 | Geng |

(Continued)

FOREIGN PATENT DOCUMENTS

| WO | WO2011049548 A1 | 4/2011 |
| WO | WO2011073813 A1 | 6/2011 |

OTHER PUBLICATIONS

Viola P. et al., "Rapid Object Detection Using a Boosted Cascade of Simple Features", Accepted Conference and Computer Vision and Pattern Recognition, 2001, pp. 1-9.

*Primary Examiner* — Seyed Azarian
(74) *Attorney, Agent, or Firm* — Michael W. Haas

(57) ABSTRACT

The present invention relates to a patient interface identification system for identifying a patient interface that is suited for a face (16) of a user (18), comprising: a receiving unit (12) for receiving a test picture (14) including the face (16) of the user (18); a database (22) for storing reference picture including faces of other users, wherein each reference picture is referenced to a patient interface advice; a processing unit (24) for comparing the received test picture (14) with at least a subset of said reference pictures stored in the database (22), wherein comparing said test picture (14) with said subset of reference pictures includes a comparison of image based features of the user's face (16) and the other users' faces; and a user interface (26) for communicating a patient interface advice including information related to a patient interface that is suited for the face (16) of the user (18), which patient interface advice is based on the comparison of said test picture (14) with the subset of reference pictures stored in the database (22).

13 Claims, 4 Drawing Sheets

(52) U.S. Cl.
CPC ........ G06K9/00248 (2013.01); G06K 9/00281 (2013.01); G06K 9/6215 (2013.01); A61M 16/0051 (2013.01); A61M 2016/0661 (2013.01); A61M 2205/502 (2013.01); A61M 2205/52 (2013.01)

(56) References Cited

U.S. PATENT DOCUMENTS

| | | |
|---|---|---|
| 2006/0235877 A1 | 10/2006 | Richard |
| 2008/0035158 A1* | 2/2008 | Pflueger .................... A61F 2/00 128/848 |
| 2008/0060652 A1* | 3/2008 | Selvarajan ............ A61M 16/06 128/206.21 |
| 2008/0078396 A1* | 4/2008 | Janbakhsh ............ A61M 16/06 128/205.25 |
| 2009/0267261 A1 | 10/2009 | Mark |
| 2011/0203594 A1* | 8/2011 | Brain ..................... A61M 16/04 128/207.15 |
| 2015/0128953 A1* | 5/2015 | Formica ............ A61M 16/0683 128/206.21 |

* cited by examiner

PATIENT INTERFACE IDENTIFICATION SYSTEM

CROSS-REFERENCE TO RELATED APPLICATIONS

This patent application claims the priority benefit under 35 U.S.C. §371 of international patent application no. PCT/IB2013/055707, filed Jul. 11, 2013, which claims the priority benefit under 35 U.S.C. §119(e) of U.S. Provisional Application No. 61/670,270 filed on Jul. 11, 2012, the contents of which are herein incorporated by reference.

FIELD OF THE INVENTION

The present invention relates to a patient interface identification system for identifying a patient interface that is suited for a face of a user. In a further aspect, the present invention relates to a corresponding method for identifying a patient interface that is suited for a face of a user. In a still further aspect, the present invention relates to a corresponding method of controlling said patient interface identification system. Still further, the present invention relates to a corresponding computer program comprising program code means for causing a computer to carry out the steps of said method when said computer program is carried out on a computer.

BACKGROUND OF THE INVENTION

Patient interfaces, such as masks in pressure support systems, are used for delivering gas to a user. Such gases like air, cleaned air, oxygen, or any modification thereof are submitted to the user (also refer to as patient) via the patient interface in a pressurized or unpressurized way.

For several chronic disorders and diseases, the usage of such a patient interface is necessary or at least advisable.

One non-limiting example of such a disease is obstructive sleep apnea or obstructive sleep apnea syndrome (OSA). OSA is usually caused by an obstruction of the upper airway. It is characterized by repetitive pauses in breathing during sleep and is usually associated with a reduction in blood oxygen saturation. These pauses in breathing, called apneas, typically last 20 to 40 seconds. The obstruction of the upper airway is usually caused by reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied with snoring. Different invasive and non-invasive treatments for OSA are known. One of the most powerful non-invasive treatments in the usage of Continuous Positive Airway Pressure (CPAP) or Bi-Positive Airway Pressure (BiPAP) in which a patient interface, e.g. a face mask, is attached to a hose and a machine that blows pressurized gas, preferably air, into the patient interface and through the airway of the patient in order to keep it open. Positive air pressure is thus provided to a patient through a hose connected to a patient interface or respiratory interface, such as a face mask, that is worn by the patient. The afore-mentioned long-term use of the patient interface is the result, since the wearing of the patient interface usually takes place during the sleeping time of the patient.

Examples for patient interfaces are:
nasal masks, which fit over the nose and deliver gas through the nasal passages,
oral masks, which fit over the mouth and deliver gas through the mouth,
full-face masks, which fit over both, the nose and the mouth, and deliver gas to both,
total-face masks, which cover the full face or substantially the full face, surrounding the nose, mouth as well as the eyes and delivering gas to the mouth and nose, and
nasal pillows (also referred to as alternative masks), which are regarded as masks as well within the scope of the present invention and which consist of small nasal inserts that deliver the gas directly to the nasal passages.

In order to guarantee a reliable operation of the device, the patient interface (mask) needs to closely fit on the patient's face to provide an air-tight seal at the mask-to-face interface. Usually, the patient interface is worn using a head gear with straps that go around the back of the patient's head. The patient interface or mask in practice usually comprises a soft cushion that is used as mask-to-patient interface, i.e. that contacts the face of the patient when the mask is worn, as well as it usually comprises a so-called mask shell building a rigid or semi-rigid holding structure for holding the cushion in place and for supplying mechanical stability to the patient interface (mask).

The cushion usually comprises one or more pads made of gel or silicone or any other soft material in order to increase the patient comfort and guarantee a soft feeling on the patient's face. The latter-mentioned mask shell usually also comprises a hose interface that is adapted for connecting the air supplying hose to the mask. Depending on the type of the mask, it may also comprise a mechanism with an additional cushion support on the forehead to balance the forces put by the mask around the airway entry features of the human face.

It is evident that a close and correct fit of the patient interface is of utmost importance for a reliable operation of the device. An incorrect fit of the patient interface may not only lead to unwanted air leaks at the mask-to-face interface, but may also cause excessive pressure points on the skin of the patient's face that again may cause unpleasant and painful red marks in the patient's face. The patient interface, therefore, needs to be accurately fitted to the individual face contours of the patient. Various types of patient interfaces exist, i.e. not only different sizes and shapes, but also different types of patient interfaces. As the anatomical features of faces differ from patient to patient, the best fitting patient interface also differs from patient to patient. In other words, an individualized fitting is required.

A mask fitting system that makes use of a simplified fitting technique is known from US 2006/0235877 A1. The mask fitting system and method described therein determine the dimensions of the patient's head with a template or a ruler. Alternatively, one or more images of the patients are captured and then the dimensions of the patient's head are manually tipped into the system using a questionnaire that has to be filled out by the patient. In any case, the absolute facial dimensions need to be either manually measured or inputted into the system by the patient filling out the questionnaire. This is, of course, bothersome and time-consuming for the user. In many practical appliances the facial dimensions cannot be measured manually (since there is no time) or no absolute dimensions of the user's face are known in advance, so that the device and method proposed in US 2006/0235877 A1 is not only disadvantageous, but can also not be applied in many practical situations.

SUMMARY OF THE INVENTION

It is an object of the present invention to provide an alternative improved system that can advise a patient about the patient interface that is best for him/her. In particular, it is an object to provide such a patient interface identification system for identifying a patient interface that is suited for the face of the user and that overcomes the above-mentioned disadvantages. The new system and method shall be easier to apply for the user, less time-consuming and practically applicable in many daily life situations.

According to an aspect of the present invention, this problem is solved by a patient interface identification system for identifying a patient interface that is suited for a face of a user, comprising:

a receiving unit for receiving a test picture including the face of the user;

a database for storing reference pictures including faces of other users, wherein each reference picture is referenced to a patient interface advice;

a processing unit for comparing the received test picture with at least a subset of said reference pictures stored in the database, wherein comparing said test picture with said subset of reference pictures includes a comparison of image based features of the user's face and the other users' faces; and a user interface for communicating a patient interface advice including information related to a patient interface that is suited for the face of the user, which patient interface advice is based on the comparison of said test picture with the subset of reference pictures stored in the database.

According to another aspect of the present invention, the above-mentioned problem is solved by a method for identifying a patient interface that is suited for a face of a user, comprising:

receiving a test picture including the face of the user;

storing reference pictures including faces of other users in a database, wherein each reference picture is referenced to a patient interface advice;

comparing the received test picture with at least a subset of said reference pictures stored in the database, wherein comparing said test picture with said subset of reference pictures includes a comparison of image based features of the user's face and the other users' faces; and communicating a patient interface advice including information related to a patient interface that is suited for the face of the user, which patient interface advice is based on the comparison of said test picture with the subset of reference pictures stored in the database.

According to a still further aspect of the present invention, the above-mentioned problem is solved by a method for controlling the above-mentioned device to carry out the steps:

receiving a test picture including the face of the user;

storing reference pictures including faces of other users in a database, wherein each reference picture is referenced to a patient interface advice;

comparing the received test picture with at least a subset of reference pictures stored in the database, wherein comparing said test picture with said subset of reference pictures includes a comparison of image based features of the user's face and the other users' faces; and communicating a patient interface advice including information related to a patient interface that is suited for the face of the user, which patient interface advice is based on the comparison of said test picture with the subset of reference pictures stored in the database.

In yet another aspect of the present invention, there is provided a computer program which comprises program-code means for causing a computer to perform the steps of the above-mentioned method when said computer program is carried out on a computer.

Preferred embodiments of the invention are defined in the dependent claims. It shall be understood that the claimed methods and the computer program have similar and/or identical preferred embodiments as the claimed system and as defined in the dependent claims.

The present invention provides a technique for identifying a suitable patient interface for the user in terms of an appropriate size, shape and/or type of the patient interface, such as a mask for pressure support ventilation systems, e.g. a CPAP-system or other mode of ventilation. The proposed device makes use of a comparison of image based features of a known person or group of persons with the same image based features of reference users from whom reference pictures are stored in a database. Thereto, facial recognition techniques are applied, e.g. by the help of a facial recognition software. The reference pictures may either be stored in a proprietary database or available through third party from images uploaded either from a web site or any portable terminal apparatus, such as e.g. a smartphone.

The solution according to the present invention compares the user's face to faces from other reference users for which user based informations relating to sizes, shapes and/or types of the patient interfaces they are using are already known. For example, the used database may include information about the best suited patient interfaces for the faces that are imaged in the reference pictures stored in the database. By analysing the test picture of the test user, deriving image based features of the test user's face from the test picture and then comparing these image based features with the reference pictures (including the reference users' faces) stored in the database, the best match (e.g. including a similarity score) may be found between the test picture and at least one of the reference pictures stored in the database. Based on this best match, the patient may be provided with a patient interface advice, i.e. an advice about which patient interface suits best for him/her. However, the patient interface advice may not only tell which mask the user need, but may also include extended information about the patient interface, e.g. how to better strap this mask on this particular face, i.e. if there are any adjustable straps junctions, how to set them for this face. On the other hand, the patient interface advice does not necessarily have to include a specific pointer to a patient interface. It may also include an information, that the other user that has been found in the picture comparison did not like a specific type of mask or that the other user prefers a certain kind of settings of a certain mask, or that the other user has tested mask A, mask B and mask C. It should be clear that the persons pictured in the database need be 'users' in the sense that it is e.g. known which patient interface each of these person uses, so that the pictures really are reference pictures that can be used to relate a person in a test picture to properties known about one or more persons in the reference pictures. The persons pictures in the database need not be patients who actually receive sleep therapy (although this probably will often be the case). Ideally the database is also updated if e.g. a person in one of the reference pictures changes to a new or another patient interface.

According to the present invention, the test picture may be compared with at least a subset of the reference pictures stored in the database. This means that some or a plurality of test pictures may be sorted out in advance, so that they are not used for the comparison. For example, if the system recognizes that the test picture includes a face of a woman, only reference pictures including female faces are used for the comparison. However, it is also possible that the test picture is compared with all reference pictures stored in the database. The term "subset" shall thus also include all reference pictures.

Furthermore, it is to be noted that the comparison may include an analysis of the received test picture and the reference pictures. Accordingly, this analysis may comprise a detection of image based features of the user's face and the other user's faces. The finally communicated patient interface may be based on said analysis and said detection.

There are known devices that also use facial images, such as pictures or photos to identify patient interface masks by using 2-D landmark identification. However, in all of the known systems and devices absolute dimensions of the facial contours need to be either known or measured manually, i.e. absolute dimensions and distances of the characteristic features of the user's face need to be available. There are also known systems that make use of portable terminal apparatus, such as e.g. smartphones, to capture such pictures or images, which use an application to perform such landmark identification in combination with linear measurements. However, the restraints of all these known systems and methods are the limited amount of information extracted from 2-D images and the lack of common datum and good point of reference in physical dimensions. The images do not allow to calibrate for meaningful measurements if no absolute dimensions of the facial contours are available in addition. The system known from US 2006/0235877 A1 mentioned in the opening paragraph thus also needs to either manually measure the facial distances on the patient itself, e.g. using a ruler or a template, or these dimensions need to be known and inputted by the patient/user him-/herself.

The present invention, instead, employs a facial recognition technique to identify the closest approximation of the face of the test user compared to faces of known patients or users taken from a database. Thus, a recommendation for a suitable patient interface (mask) provided by the system is purely based on known facts about the identified reference persons, which facts are stored in the database. For example, individual A's image is found to be a closest resemblance to individual B from the database by the facial recognition software. If B is a user of a certain type of patient interface (mask), it is likely that the same patient interface also fits to the face of individual A. Such user-based database can be managed anonymously by a service provider or it can be managed by sponsor sites through certain social networks or other user groups. The facial recognition and comparison of the image based features of the user's face may, for example, make use of the fact that small faces look different than big faces. Thus, the test picture may be compared to the mentioned reference pictures within the database by analysing and comparing characteristic face features, also refer to as image based features. A user interface may then communicate a patient interface advice to the user to identify a suitable patient interface. In other words, the patient interface gives a corresponding mask advice to the user about which type, shape and/or size fits best to him/her. The user interface may, for example, be a monitor, such as a monitor of a PC (for visual communication), however the advice may also be communicated to the user through any type of loudspeaker (as an audible advice).

It is to be noted, that the term patient interface advice may include any advice that is related to and includes or comprises information about a size, a shape and/or a type of the patient interface that is recommended to the user. However, the patient interface advice does not necessarily need to include information that directly gives a certain and distinctive recommendation to a specific type of user mask. The patient interface advice may, for example, also include information or a recommendation not to use a specific type of patient interface (mask), or include information that the reference user that has been found to most strongly resemble to the test user (the test user's face) has had problems with one type of mask or preferred a different type of mask. In any way, independent on the specific type of information that is delivered through the patient interface advice, the patient interface advice should help the user to select an appropriate patient interface that suits best for him/her.

According to an embodiment of the present invention, the comparison of the image based features of the user's face and the other users' faces includes a determination of an angle ratio or a distance ratio between anatomical landmarks within the test picture and the reference pictures and a comparison of said angle ratio or distance ratio in the test picture with the corresponding angle ratio or distance ratio in each of the subset of reference pictures.

It is to be noted that also the combination of one or more angle ratios and distance ratios can be used for the comparison of the test picture and the reference pictures stored in the database. The anatomical landmarks may be related to a position of an eye, a nose or a mouth or parts of it. Accordingly, the anatomical landmarks identified in the test pictures and in the reference pictures can indicate a position of an eye, a nose or a mouth or parts of it.

Since usually no absolute dimensions are known or available from the pictures (the test pictures as well as the reference pictures) such absolute dimensions are indirectly deduced from the plane 2D-pictures, i.e. without measuring the pictures, by calculating ratio of dimensions/angles. In order to calculate these ratios, no absolute dimensions need to be known or available. Nevertheless, these ratios are indicators for certain face forms and may also give a hint to the size of one's face. As already mentioned, these ratios, e.g. the aspect ratio of the distance between the eyes and the distance from the nose to the mouth, may be different for small and big faces. The presented patient interface identification system intelligently derives size and shape indicators that offer valuable clues about the face contours of the user. Said indicators may be easily compared, i.e. comparing the indicators deduced from the test picture with the indicators deduced from each of the reference pictures in the database. One exemplary indicator may also be the aspect ratio of the mouth heights to the mouth width.

Instead of comparing said angle ratio or distance ratio in the test picture with the corresponding angle ratio or distance ratio in each of the subset of reference pictures, said angle ratio or distance ratio in the test picture may also be compared with the corresponding angle ratio or distance ratio in all reference pictures stored in the database.

According to a further embodiment of the present invention, the processing unit is adapted to determine the patient interface advice based on a best match between said angle ratio or distance ratio in the test picture with the corresponding angle ratio or distance ratio in one of the reference pictures.

This best match can, for example, be found by applying a least square method. In other words, according to an embodiment of the present invention said best match is determined by calculating the least square between said at least one angle ratio or distance ratio in the test picture and the corresponding at least one angle ratio or distance ratio in each of the subset of reference pictures. Such a calculation may help to compute a similarity score between the test picture and each of the pictures from the database. In this way, the reference picture with the closest resemblance to the test picture can easily be found.

Instead of analyzing the angle and distance ratios, intensity gradients and relative intensity gradients in the pictures may also be used as indicators for the comparison. According to a further embodiment of the present invention, the comparison of said image based features of the user's face and the other users' faces include a determination of intensity gradients at predetermined positions with respect to anatomical landmarks within the test picture and the reference pictures and a comparison of said intensity gradients in the test picture with the corresponding intensity gradients in each of the subset of reference pictures. It is to be noted that it is also possible, and even desirable in several case, to analyse the pictures based on the mentioned intensity gradients as well as based on the mentioned angle and distance ratios, i.e. the above-mentioned techniques may be combined. In this case, the processing unit is adapted to determine the patient interface advice based on a best match between said angle ratio, said distance ratio and/or said intensity gradients in the test picture with the corresponding angle ratio, distance ratio and/or intensity gradients in one of the reference pictures.

According to a further embodiment of the present invention, the processing unit is further adapted to detect an area of interest in the test picture and each of the subset of reference pictures, to crop the test picture and the reference pictures to the area of interest and to re-size the test picture and the reference pictures to a common predefined size, before analysing and comparing the test picture and the reference pictures.

Such a cropping and re-sizing helps to form a common basis for the analysis. Even if the test picture and the reference picture stored in the database are taken from different distances or include different sizes or the faces therein have different sizes, the pictures are in this way brought to a common format. This especially helps for analysing the pictures as mentioned above and to identify the image based features, i.e. the mentioned angle and distance ratios of the anatomical features within the pictures. Thereby, it is preferred that the area of interest includes the face of the user within the test picture or a face of the other users within the reference pictures, respectively.

After re-sizing and cropping the pictures in the above-mentioned way, all faces/areas of interest should have the same size and are thus easier to compare with each other. Independent of how the pictures were originally taken, all pictures then look like pass-photos. This significantly improves the picture comparison and thus eases to identify the reference picture that has the closest resemblance to the test picture, i.e. to identify a known reference face within the database that has the most resemblance to the face of the user that searches for a suitable patient interface (mask).

According to a further embodiment of the present invention, the processing unit is further adapted to convert the test picture and the reference pictures to greyscale pictures, before analysing and comparing the test picture and the reference pictures.

Preferably, this conversion to greyscale is made after re-sizing and cropping the pictures. However, it may be also done in advance. It is to be noted that, of course, only colour images/pictures need to be converted to greyscale, whereas pictures already received as greyscale images do not need to be converted anymore. Greyscale pictures allow to more easily detect the face features inside the region of interest. However, it is to be noted that the system would also work without converting the pictures to greyscale images, i.e. simply by comparing colour images, even though the colours within the pictures could impede the analysis and comparison. Thus, greyscale images are generally preferred.

According to a further embodiment of the present invention, the user interface is adapted to communicate a patient interface advice to identify a patient interface that is suited for the face of the user in a hierarchical order starting from a best match patient interface to a worst match patient interface.

In other words, the results are presented to the user in the form of a list, which list is ordered hierarchically according to the similarity score that has been computed for the comparison of the test picture and the reference pictures from the database. In still other words, the database entries are ranked according to the computed similarity score, and the first few entries with the minimal values of the similarity metric can be identified and extracted from the database. The entries may then be shown to the user (e.g. the patient) or to a doctor or technician that supports the user to find the appropriate mask that fits best to the user's face. The entries may, for example, be shown with the similarity scores in the order from most to least similar. The similarity scores can be shown in percents and/or normalized such that they sum up to 100%.

According to a further embodiment of the present invention, the system may further comprise a picture capturing unit for capturing the test picture of the face of the user. This picture capturing unit may, for example, be realized by a simple photo or video camera, with which regular 2D-pictures may be taken. The test pictures taken by the picture capturing unit may be connected to the remaining components of the proposed system, e.g. to the processing unit, either hard-wired or via a wireless connection.

The above-described patient interface identification system may, for example, also be integrated into a smartphone that is equipped with a photo camera. The necessary software may, for example, be realized as an Iphone app or an app for any other smartphone or computer. However, it is to be noted that this is only an example and that the patient interface identification system may also be integrated into a computer, such as a PC or any other computing device.

BRIEF DESCRIPTION OF THE DRAWINGS

These and other aspects of the invention will be apparent from and elucidated with reference to the embodiment(s) described hereinafter. In the following drawings FIG. 1 schematically illustrates a first embodiment of the patient interface identification system according to the present invention.

DETAILED DESCRIPTION OF THE INVENTION

Figure 1:
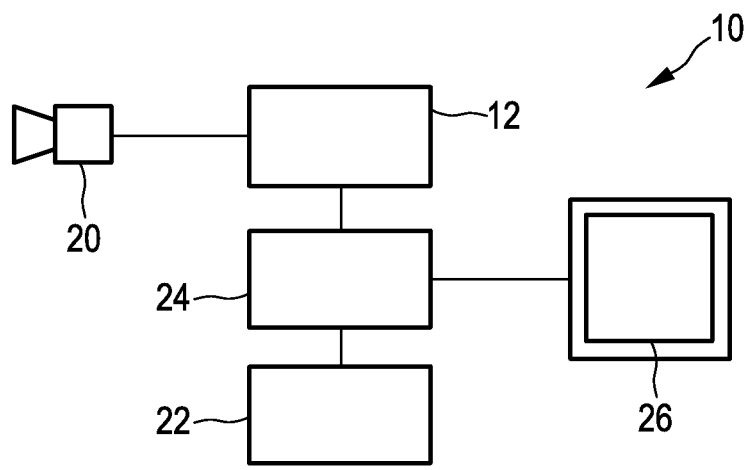

FIG. 1 shows an embodiment of a patient interface identification system for identifying a patient interface that is suited for a face of a user, which system may also be referred to as a mask fitting system. The proposed system is therein in its entirety denoted with reference numeral 10. According to the illustrated embodiment, the patient interface identification system 10 comprises a receiving unit 12 for receiving a test picture 14 (see e.g. FIG. 4), which test picture 14 includes a face 16 of a user 18. The receiving unit 12 may, for example, be realized as a connection interface that is suitable for receiving or downloading pictures to the system 10. Examples may be a USB-interface, firewire interface, a Bluetooth interface, a wireless LAN interface or an infrared interface. However, the receiving unit may also be a simple interface that is connected to the Internet for downloading the test picture 14 from any external database. Even further, the receiving unit 12 may be an internal or external connection, e.g. an integrated circuit connection or a wire, that is connected to a capturing unit 20 for capturing the test picture 14 of the face 16 of the user 18.

The capturing unit 20 may be realized as a 2D-camera or video camera or any other device that is suitable for taking two dimensional pictures. It is to be noted, that the capturing unit 20 is not necessarily needed for the system 10, as the test picture 14 may also be taken with an external device and then transferred to the system 10 via the receiving unit 12.

The patient interface identification system 10 further comprises a database 22 for storing reference pictures including faces of other users. Furthermore, the patient interface identification system 10 includes a processing unit 24 for analysing the received test picture 14 and the reference pictures stored in the database 22 and for comparing said test picture 14 with the reference pictures stored in the database 22. The processing unit 24 analyses and compares image based features of the user's face 16 and the other users' faces within the test picture 14 and the reference pictures stored in the database, respectively. The processing unit 24 is furthermore adapted to determine a patient interface advice based on said analysis and comparison of the image based features of the user's face and the other users' faces. The processing unit 24 may make use of a facial recognition software that compares the face 16 within the test picture 14 to faces of known persons which are imaged in the reference pictures stored in the database 22. These reference pictures may, for example, be available through third party from pictures uploaded either from a website or any other portable terminal apparatus, e.g. a smartphone. Thus, the database 22 itself does not necessarily have to be an internal database that is locally integrated into the device, but also may be an external database 22 available through the Internet or any other network.

The processing unit 24, by analysing and comparing the test picture 14 and the reference pictures stored in the database 22, identifies the closest approximation of other users' faces in the reference pictures with the face 16 included in the test picture 14 of the user 18. In other words, the processing unit 24 is adapted to identify a reference picture stored in the database 22 that most closely resembles, i.e. has the most similarities with the test picture 14, in order to find a face within the database 22 that is, from an anatomical point of view, similar to the face 16 of the user 18 shown in the test picture 14. Based on this picture analysis and picture comparison a patient interface advice is determined, e.g. a recommendation for a certain type, size and shape of a mask that fits best to the face 16 of the user 18 is determined/calculated. This mask usage recommendation is purely made based on known facts about the other users that are pictured in the reference pictures. For example, individual A's image is found to be a closest resemblance to individual B from the database 22 by the processing unit 24 using the facial recognition software. If B is a user of a certain type of mask, it is likely that A can put on this mask as well.

The patient interface advice, also referred to as mask advice or mask usage advice, may then be communicated to the user via a user interface 26. The user interface 26 may, for example, be realized as a screen or a display on which the determined mask advices are visually illustrated. However, the user interface 26 may also be realized as a loudspeaker or any other type of sound-producing device that outputs the mask advices in audible form.

Figure 2:
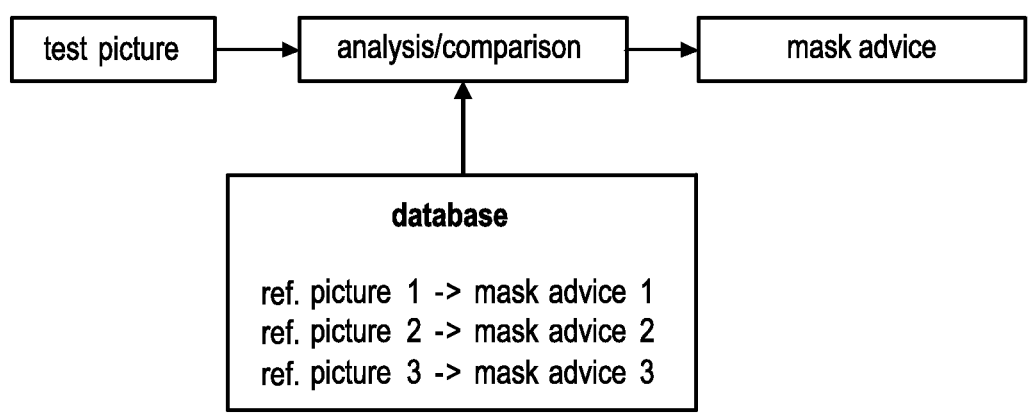
FIG. 2 shows a process diagram to visualize a logic that is applied according to an embodiment of the patient interface identification system according to the present invention.

FIG. 2 again illustrates the principle of the patient interface identification system 10 and the proposed method according to the present invention.

This process diagram illustrates the principle as follows: First, a test picture 14 of the patient's face 16 (see e.g. FIG. 4) is captured by means of a camera, such as a webcam, a smartphone camera, or any other type of regular 2D-camera. When in the loop, the test picture 14 is compared with every reference picture in the database 22. For each comparison, a similarity score is computed between the test picture 14 and the reference picture from the database 22. Then, the database entries are ranked according to the computed similarity score, and the first few entries with the minimal values of the similarity metric are identified and extracted from the database 22. The entries are then shown to the user together with the similarity scores in the order from most to least similar. The similarity scores can be shown in percents and normalized such that they sum up to 100%. In this way, a list may be produced that includes information about which type, size or shape of mask could be suitable for the user. The recommendation for a suitable patient interface (mask) provided by the system is purely based on known facts about the identified reference persons, i.e. without having to manually or automatically measure absolute dimensions within the face of the user.

In the following, the method and principle of the present invention shall be described according to an exemplary embodiment and with reference to FIGS. 3 to 7.

Figure 3:
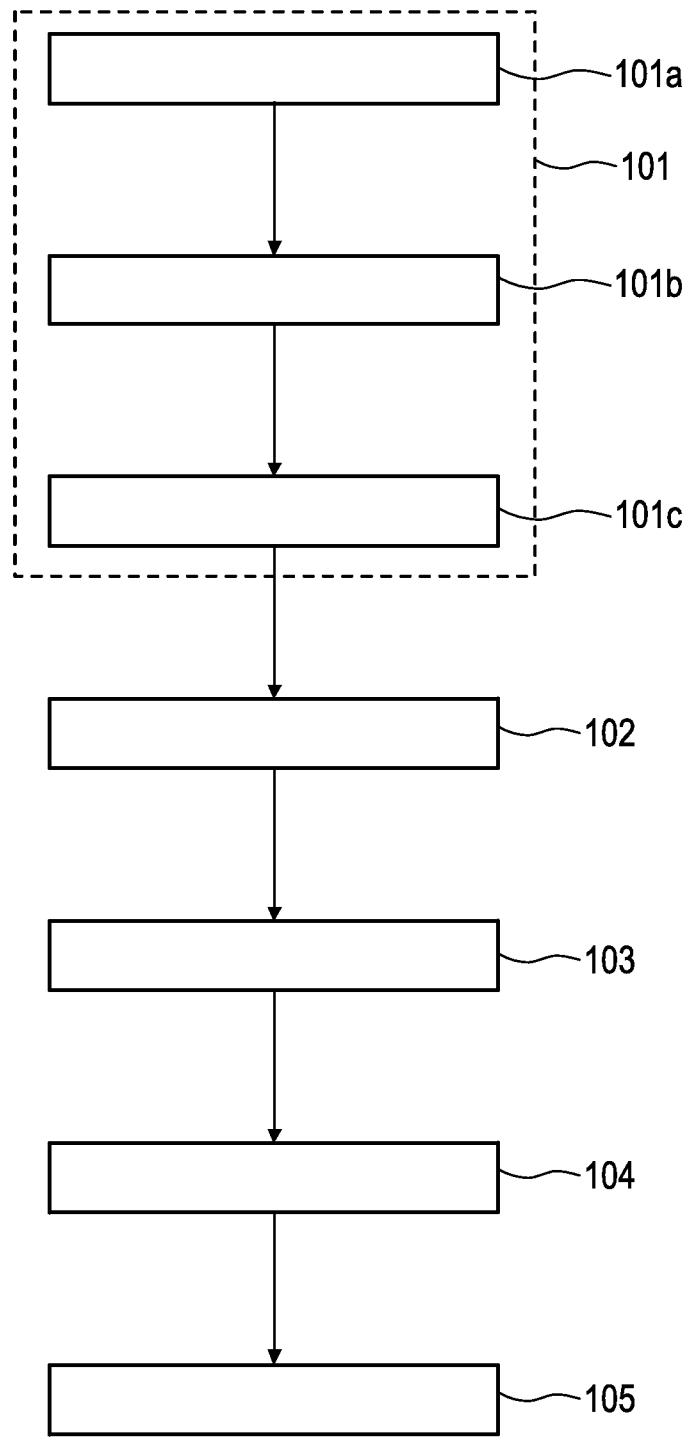
FIG. 3 shows a process diagram schematically illustrating an embodiment of a method for identifying a patient interface according to the present invention.

FIG. 3 illustrates a flow-chart of a method according to an embodiment of the present invention. The proposed method for identifying a patient interface that is suited for a face of a user basically comprises five method steps 101-105. The step of receiving the test picture is therein not explicitly illustrated again.

The first step may be denoted as pre-processing step 101. This pre-processing step 101 includes three sub-steps: A face detection step 101a, a cropping and re-sizing step 101b and a colour conversion step 101c. The pre-processing step 101 is applied to the test picture 14 as well as to the reference pictures stored in the database 22.

In the face detection step 101a, an image based feature detection algorithm is applied, for example a Viola-Jones algorithm known from Viola and Jones, "Rapid Object Detection Using a Boosted Cascade of Simple Features", in Computer Vision and Pattern Recognition, 2001, which is herein fully incorporated by reference. It is to be noted that also other or analogue algorithms may be applied in the face detection step 101a.

Some mobile devices/smartphones allow to tap on the area of interest in the active camera image during the photo acquisition. Then the mobile devices/smartphone adjusts the focus/exposure to maximize the image quality in the area of interest. In some embodiments the evoking of this feature can be used to limit the search area for the face to the indicated area of interest.

Figure 4:
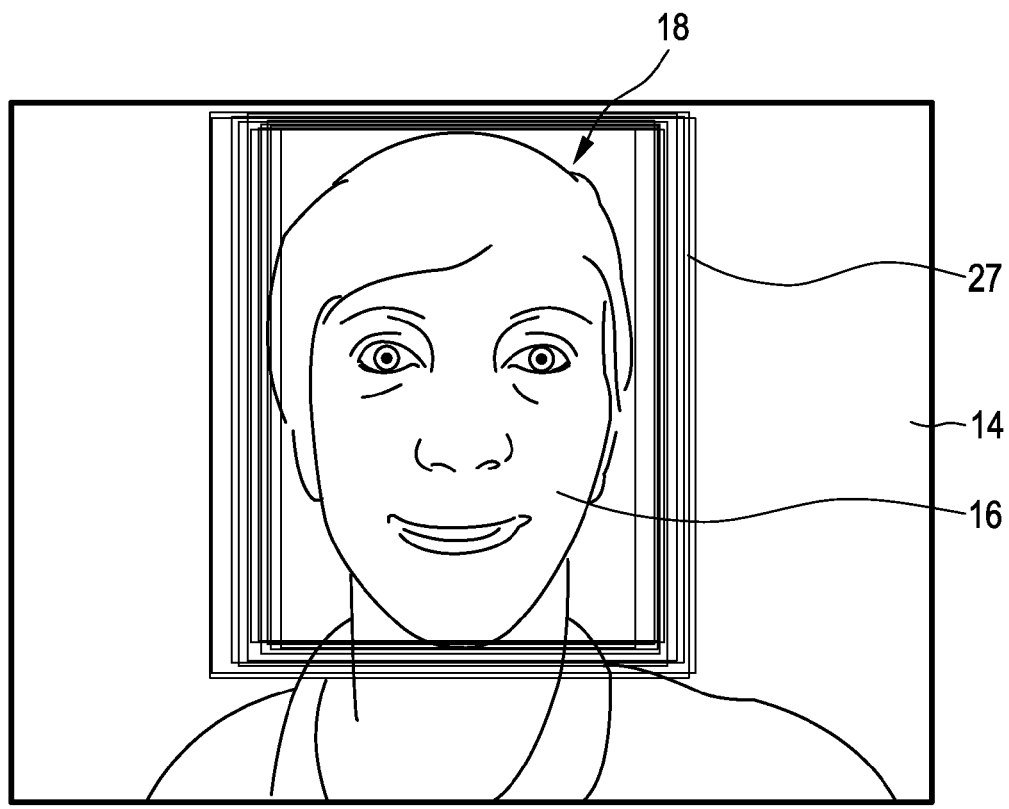
FIG. 4 shows an exemplary test picture of a user.

As it is schematically illustrated in FIG. 4, the face detection algorithm returns a set of rectangles 27 around the probable face detected different scale ratios. In other words, an area of interest is detected in each of the test picture 14 and the reference pictures from the database 22. Then, the rectangle positions 27 are averaged to determine a robust position of the face 16 of the test user 18 on the image 14.

Figure 5:
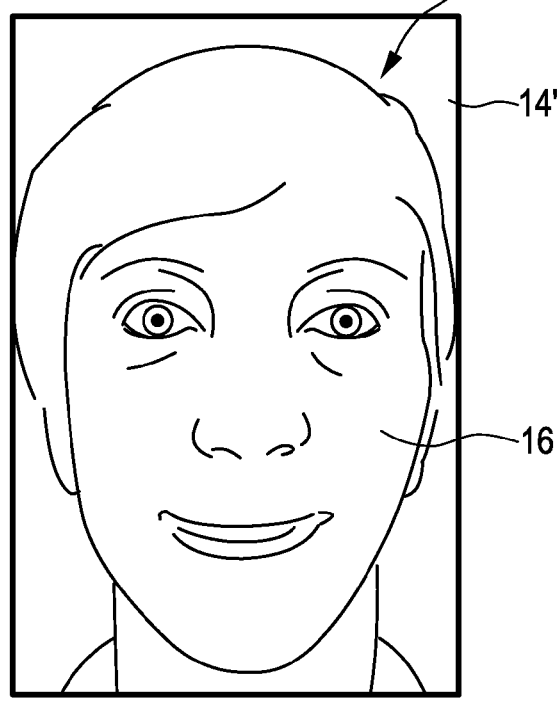
FIG. 5 shows the test picture of the user after having been cropped and re-sized.

In the cropping and re-sizing step 101b, the averaged rectangular area 27 is cropped (e.g. together with 0%-50% margin around the rectangle 27) from the image 14 and scaled to a certain pre-defined size. The result of this cropped and re-sized image 14' is shown in FIG. 5. Such a cropping and re-sizing helps to form a common basis for the analysis. Even if the test picture and the reference picture stored in the database are taken from different distances or include different sizes or the faces therein have different sizes, the pictures are in this way brought to a common format.

In the colour conversion step 101c, the test picture/image 14 is then converted to a greyscale image. It is to be understood that, of course, this colour conversion step 101c only occurs if the originally delivered/captured test picture 14 is a coloured image. Otherwise, this colour conversion step is not necessary.

Figure 6:
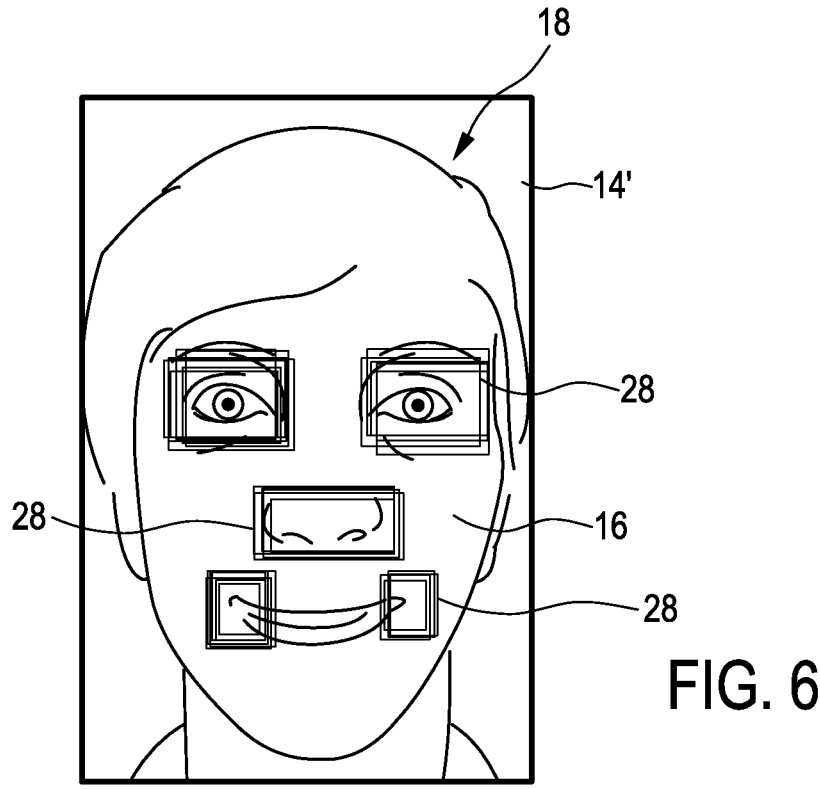
FIG. 6 shows the test picture of FIG. 5 including identified facial landmarks within the picture.

The next step 102, also referred to as landmark detection step 102, comprises a detection of face features inside the region of interest. For this step, image face feature detection algorithms can be applied. FIG. 6 shows a typical result for a boosted cascade detection, based on Haar-like features, which are separately trained for detection of eyes, nose and mouth corners. The face detection algorithm returns a set of rectangles 28 around the probable face landmarks detected at different scale ratios (see FIG. 6). These rectangle positions are then averaged to determine a robust position of the facial landmarks on the cropped and re-sized test picture 14'.

Figure 7:
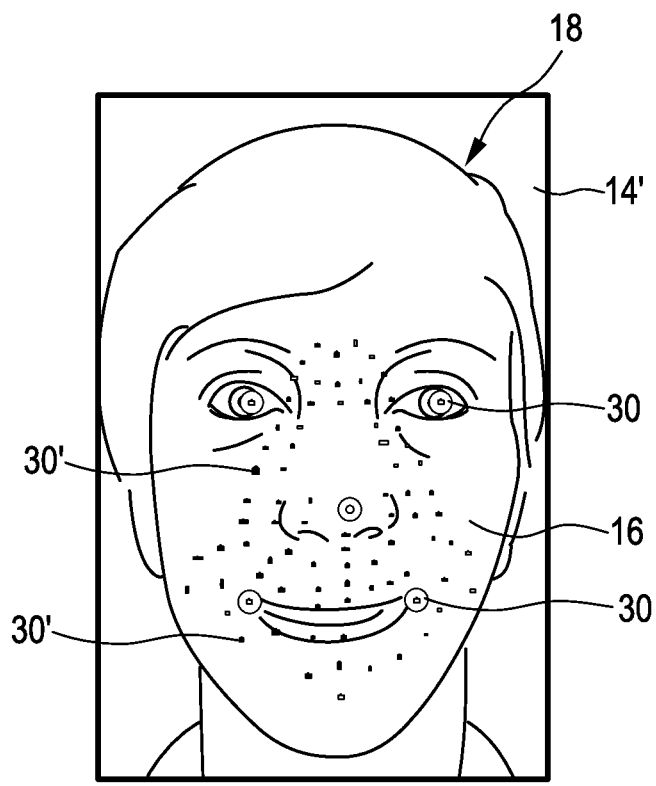
FIG. 7 shows the test picture of FIG. 5 with extracted image based features.

During the next method step 103, also referred to as feature extraction step 103, two types of features are preferably extracted from the cropped and re-sized test picture 14': 1.) landmark angles and distance ratios in all possible combinations, 2. local image features extracted around the nasal and mouth area (see FIG. 7).

In FIG. 7, big dots 30 refer to landmarks located in the previous step, and small dots 30' are relative positions (with respect to landmarks) for the local image features extractions. The local features can be local image gradients identified in the test picture 14'. This landmark identification thus allows for calculating image based features, such as e.g. the aspect ratio of the distance between the eyes and the width of the mouth or the nose. Of course, many different other ratios can be computed that are indicative and offer valuable clues to the form of the face and the size of the characteristic face features. It thus allows to indirectly calculating facial dimensions directly from the test picture 14', even though the exact absolute dimensions are not known.

The derived image features may then result in one or more characteristic feature vectors. These feature vectors are extracted from both greyscale pictures, from the test picture 14' as well as from all reference pictures stored in the database 22.

The feature vectors extracted in step 103 are usually high dimensional and can contain a lot of redundant irrelevant information. Therefore, a feature vector reduction step 104 is applied. In this feature vector reduction step 104, the dimensionality of the feature vectors is reduced by multiplication with the matrix of proper dimension:

$$rv_t = M \times v_t, rv_d = M \times v_d$$

where $rv_t$ is a reduced feature vector for the test image, and $rv_d$ is a reduced feature vector for the database image, and matrix M has a dimension k×n, k>>n, and matrix M is obtained by leave-one-out Least Mean Square training of the database for the best advice.

Finally, in a so-called comparison step 105, the error between the test picture 14' and the database/reference picture may be defined as l2-norm between the reduced feature vectors, i.e.:

$$e = \frac{1}{n}\sum_{i=1}^{n}|rv_t(i) - rv_d(i)|^2$$

The similarity score can be defined as a function inverse proportional to the error between the two pictures:

$$\text{score} = \frac{100\%}{c+e},$$

where c>0 is some calibration constant.

Finally, the user is thus provided with a list of mask advices which are mapped to reference pictures stored in the database 22 that have been found to most closely resemble the face/face contours/facial dimensions/facial characteristics of the test picture 14. The latter mentioned formulas does not imply that the scores will sum up to 100%. Therefore, in some embodiments, one could have an optional normalization/scaling step, after which the scores will sum up to 100%. This supports the user in finding a suitable patient interface in an easy and fast forward manner.

In summary, the invention thus proposes a technique that allows to identify a best match patient interface (mask) by simply taking a regular 2D-picture of the patient and then applying facial feature detection and comparing these image based features to pictures of known users in database. Thereto, no extensive measurements have to be made directly on the patient, i.e. on the patient's face and no cost-intensive 3D-scanning is necessary.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A patient interface identification system for identifying a patient interface that is suited for a face of a user, comprising:
a processor structure for receiving a test picture including the face of the user;
a database storing reference pictures including faces of other users, wherein each reference picture is referenced to a patient interface advice including information about a patient interface that is suited for the face imaged in said particular reference picture;

a processor unit structured for comparing the received test picture with at least a subset of said reference pictures stored in the database, wherein comparing said test picture with said subset of reference pictures includes a comparison of image based features of the user's face and the other users' faces; and a user interface structured for communicating a patient interface advice including information related to a patient interface that is suited for the face of the user, which patient interface advice is based on the comparison of said test picture with the subset of reference pictures stored in the database, and wherein the comparison of said image based features of the user's face and the other users' faces includes: (a) a determination of an angle ratio or a distance ratio between anatomical landmarks within the test picture and the reference pictures and a comparison of said angle ratio or distance ratio in the test picture with the corresponding angle ratio or distance ratio in each of the subset of reference pictures, or (b) a determination of intensity gradients at predetermined positions with respect to anatomical landmarks within the test picture and the reference pictures and a comparison of said intensity gradients in the test picture with the corresponding intensity gradients in each of the subset of reference pictures.

2. A patient interface identification system according to claim 1, wherein the processing unit is adapted to determine the patient interface advice based on a best match between said angle ratio or distance ratio in the test picture with the corresponding angle ratio or distance ratio in one of the reference pictures.

3. A patient interface identification system according to claim 1, wherein said best match is determined by calculating the least square between said angle ratio or distance ratio in the test picture and the corresponding angle ratio or distance ratio in each of the subset of reference pictures.

4. A patient interface identification system according to claim 1, wherein the anatomical landmarks are related to a position of an eye, a nose or a mouth or parts of it.

5. A patient interface identification system according to claim 1, wherein the processing unit is further adapted to detect an area of interest in the test picture and each of the subset of reference pictures, to crop the test picture and the reference pictures to the area of interest and to re-size the test picture and the reference pictures to a common predefined size, before analysing and comparing the test picture and the reference pictures.

6. A patient interface identification system according to claim 5, wherein the area of interest includes the face of the user within the test picture or a face of the other users within the reference pictures, respectively.

7. A patient interface identification system according to claim 1, wherein the processing unit is further adapted to convert the test picture and the reference pictures to greyscale pictures, before analysing and comparing the test picture and the reference pictures.

8. A patient interface identification system according to claim 1, wherein the patient interface advice includes information about a size, a shape and/or a type of the patient interface that is recommended to the user.

9. A patient interface identification system according to claim 1, wherein the user interface is adapted to communicate a patient interface advice to identify a patient interface that is suited for the face of the user in a hierarchical order starting from a best match patient interface to a worst match patient interface.

10. A patient interface identification system according to claim 1, further comprising a picture capturing unit for capturing the test picture of the face of the user.

11. A method of controlling a device according to claim 1 to carry out the steps of:

receiving a test picture including the face of the user;

storing reference pictures including faces of other users in a database, wherein each reference picture is referenced to a patient interface advice including information about a patient interface that is suited for the face imaged in said particular reference picture;

comparing the received test picture with at least a subset of reference pictures stored in the database, wherein comparing said test picture with said subset of reference pictures includes a comparison of image based features of the user's face and the other users' faces; and communicating a patient interface advice including information related to a patient interface that is suited for the face of the user, which patient interface advice is based on the comparison of said test picture with the subset of reference pictures stored in the database.

12. Method for identifying a patient interface that is suited for a face of a user, comprising:

receiving in a processor structure through an interface coupled to a processing unit a test picture including the face of the user;

storing reference pictures including faces of other users in a database coupled to the processing unit, wherein each reference picture is referenced to a patient interface advice including information about a patient interface that is suited for the face imaged in said particular reference picture;

comparing in the processing unit the received test picture with at least a subset of said reference pictures stored in the database, wherein comparing said test picture with said subset of reference pictures includes a comparison of image based features of the user's face and the other users' faces; and communicating from a hardware visual or audio user interface a patient interface advice including information related to a patient interface that is suited for the face of the user, which patient interface advice is based on the comparison of said test picture with the subset of reference pictures stored in the database, and wherein comparing the image based features of the user's face and the other users' faces includes: (a) a determination of an angle ratio or a distance ratio between anatomical landmarks within the test picture and the reference pictures and a comparison of said angle ratio or distance ratio in the test picture with the corresponding angle ratio or distance ratio in each of the subset of reference pictures, or (b) a determination of intensity gradients at predetermined positions with respect to anatomical landmarks within the test picture and the reference pictures and a comparison of said intensity gradients in the test picture with the corresponding intensity gradients in each of the subset of reference pictures.

13. A non-transitory computer readable medium encoded with a computer program comprising program code means for causing a computer to carry out the steps of the method as claimed in claim 12 when said computer program is carried out on the computer.

* * * * *